United States Patent [19]
Nettekoven

[11] Patent Number: 5,496,270
[45] Date of Patent: Mar. 5, 1996

[54] TRI-TUBULAR SUCTION IRRIGATION DEVICE

[75] Inventor: William S. Nettekoven, Sandy, Utah

[73] Assignee: MegaDyne Medical Products, Inc., Draper, Utah

[21] Appl. No.: 312,479

[22] Filed: Sep. 26, 1994

[51] Int. Cl.[6] .................................................. A61M 1/00
[52] U.S. Cl. ......................... 604/30; 604/33; 604/249; 604/256
[58] Field of Search ............................. 604/30, 33, 34, 604/249, 250, 256, 258, 259, 902; 251/4, 7

[56] References Cited

U.S. PATENT DOCUMENTS

| | | |
|---|---|---|
| 790,353 | 5/1905 | Estlingen . |
| 2,624,364 | 1/1950 | Detlefsen . |
| 2,643,848 | 6/1953 | Hoffmann . |
| 4,425,113 | 1/1984 | Bilstad . |
| 4,425,116 | 1/1984 | Bilstad et al. . |
| 4,428,745 | 1/1984 | Williams . |
| 4,524,802 | 6/1985 | Lawrence et al. . |
| 4,627,833 | 12/1986 | Cook . |
| 4,713,051 | 12/1987 | Steppe et al. . |
| 4,821,996 | 4/1989 | Bellotti et al. . |
| 4,852,551 | 8/1989 | Opie et al. . |
| 4,946,434 | 8/1990 | Plaisted et al. . |
| 5,195,959 | 3/1993 | Smith . |
| 5,195,960 | 3/1993 | Hossain et al. . |
| 5,219,327 | 6/1993 | Okada . |
| 5,230,704 | 7/1993 | Moberg et al. ............................ 604/34 |
| 5,254,083 | 10/1993 | Gentelia et al. .......................... 604/34 |
| 5,282,787 | 2/1994 | Wortrich . |
| 5,322,503 | 6/1994 | Desai ....................................... 604/33 |
| 5,354,291 | 10/1994 | Bales et al. ............................... 604/30 |

FOREIGN PATENT DOCUMENTS 4208054 of 1992 Germany .

*Primary Examiner*—John D. Yasko
*Assistant Examiner*—Laird J. Knights
*Attorney, Agent, or Firm*—John L. Sigalos

[57] ABSTRACT

A suction-irrigation device having a hinged reusable housing enclosing a disposable tri-tubular cassette that is replaced each time the device is used. The three tubes of the tri-tubular cassette provide respectively for irrigation fluid, suction and instrument pass through. A pair of symmetrically positioned trumpet-type actuators are equipped with friction-reducing rollers and are disposed in a wedging configuration to selectively impart squeezing action on the irrigation fluid and suction tubes, thereby providing control that is provided for ambidextrous use, that is, it is equally adapted for left and for right handed use.

20 Claims, 3 Drawing Sheets

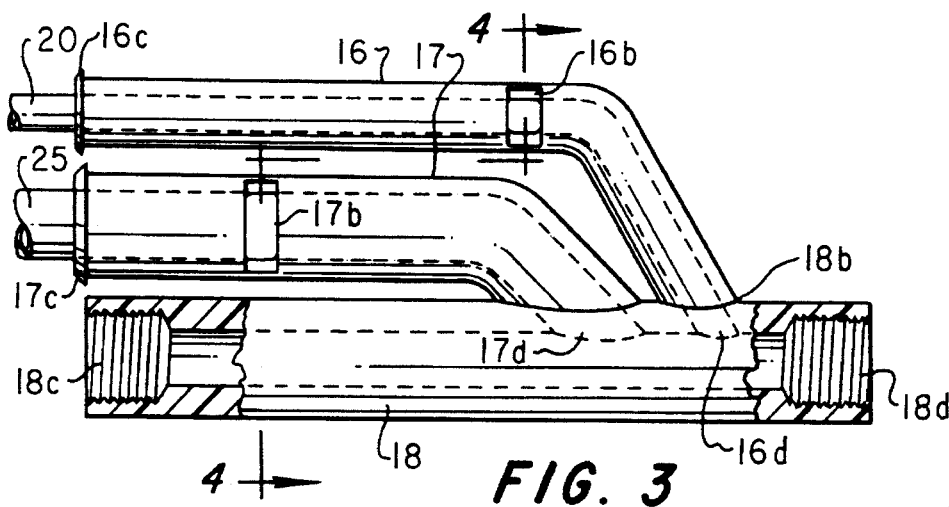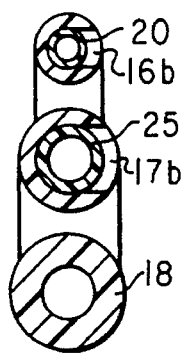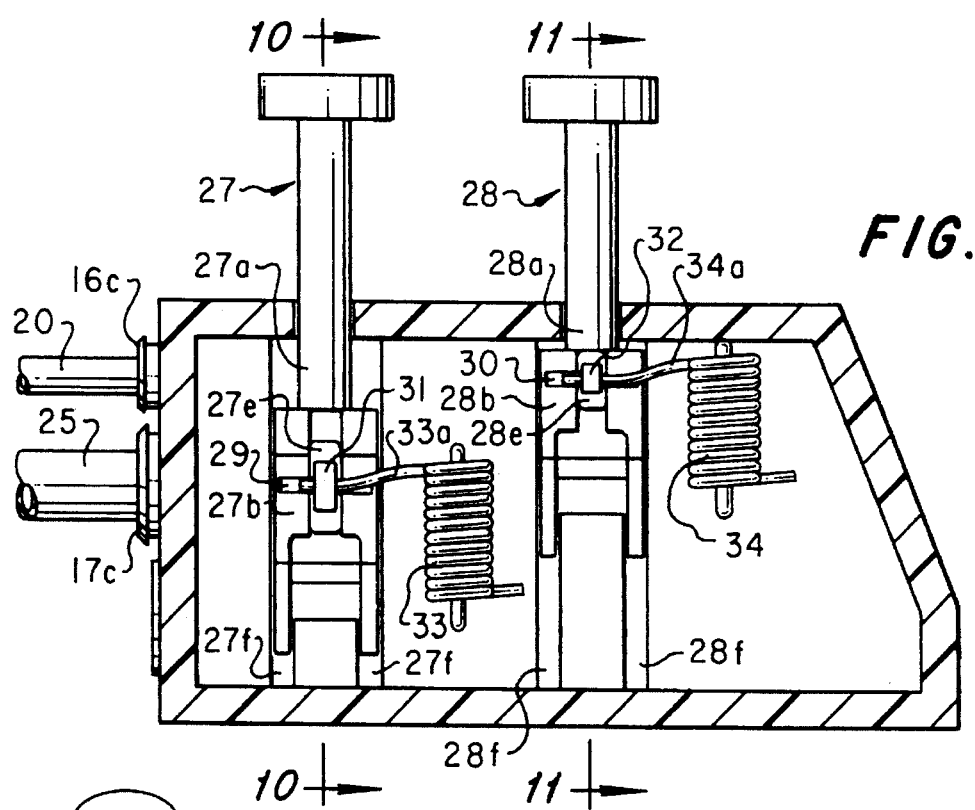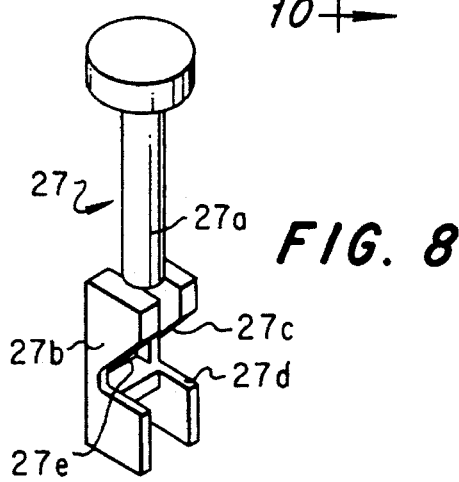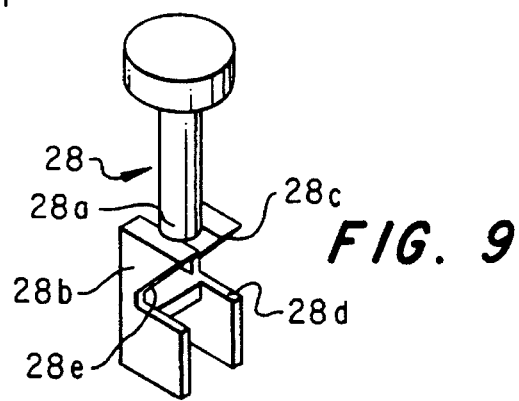

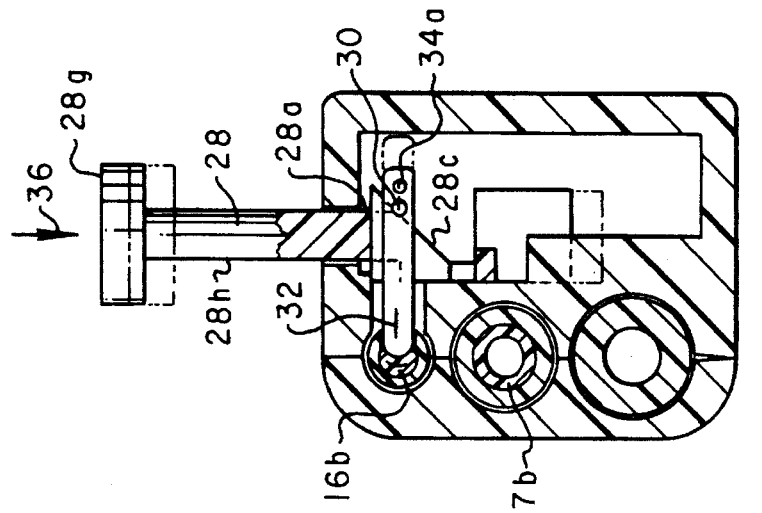
FIG. 10
FIG. 11
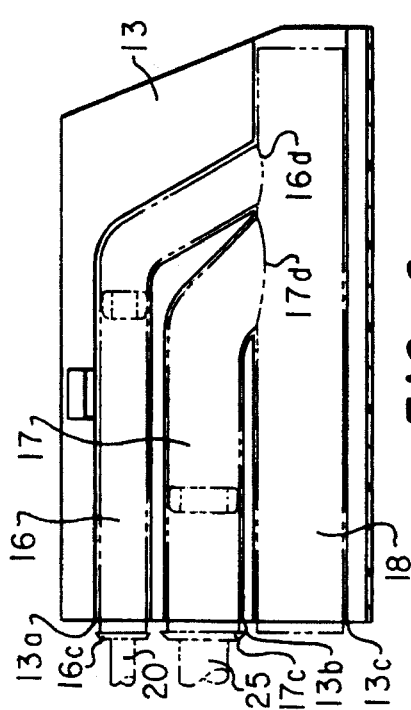
FIG. 6
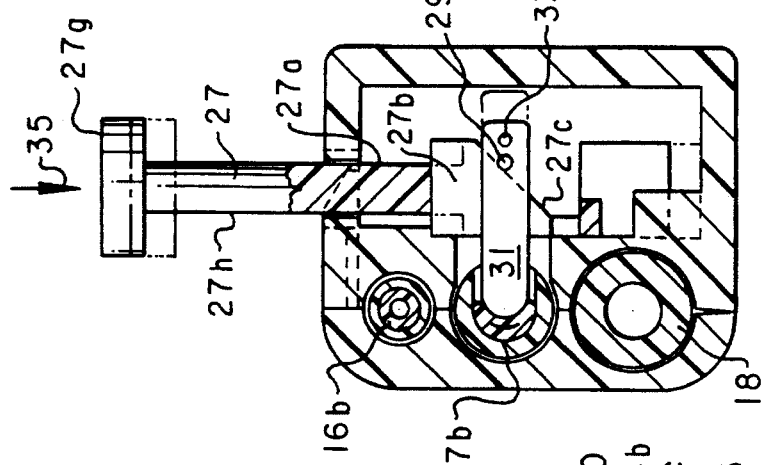
FIG. 7

TRI-TUBULAR SUCTION IRRIGATION DEVICE

This invention relates to suction-irrigation devices and more particularly to such devices that are specially adapted for use in performing medical procedures.

BACKGROUND OF THE INVENTION

As surgical knowledge and techniques have progressed, there has been a corresponding trend toward size reduction of surgical incisions and invasive instruments, thus decreasing patient trauma and contributing to rapidity of patient recovery. This has led to the practice of endoscopy including laparoscopic surgical procedures which are characterized by one or more very small incisions or openings as contrasted with the previously conventional large incisions. Since corrective procedures are conducted through very small incisions or other openings, it has become important to provide for multiple techniques/procedures to be performable by a single very small instrument. Examples of such multiple techniques/procedures include irrigation, suction and deployment of one or more surgical electrodes.

Recent discoveries of the danger of transmitting deadly diseases such as AIDS have led to heightened awareness of the importance of complete and thorough sterilization. Although it is possible to clean and sterilize suction-irrigation devices both exteriorally and interiorally, the cleaning and sterilization procedures have been time consuming and costly. Accordingly, there has been a need for continuing improvements in suction-irrigation devices that provide the needed multiple capabilities while being easily and quickly cleaned and prepared for re-use.

Multi-element suction-irrigation devices have heretofore been proposed, illustrative of which are those described in U.S. Pat. Nos. 790,353 granted to E. S. Estlingen on May 23, 1905; 2,624,364 granted to G. C. Detlefsen on Jan. 6, 1953; 4,425,113 granted to Arnold C. Bilstad on Jan. 10, 1984; 4,425,116 granted to Arnold C. Bilstad et al. on Jan. 10, 1984; 4,852,551 granted to Erie A. Opie et al. on Aug. 1, 1989; and 5,195,959 granted to Paul C. Smith on Mar. 23, 1993. Collectively, these patents disclose various forms of squeeze control, multi-passage conduits, disposable inserts, trumpet-type control valves and hinged housings. However, while these patents individually suggest various ones of the foregoing features, they do not singly or in combination teach or suggest a multi-passage suction-irrigation device that includes all of those features while being adapted for equally easy use in either the right or left hand of the user.

BRIEF SUMMARY OF THE INVENTION

The improved suction-irrigation device according to the invention hereof includes a hinged housing for ease of opening, a contoured interior adapted for receiving a disposable tri-tubular cassette that is discarded after each use, a plurality of improved trumpet type piston-operated plungers in combination with rollers and wedging surfaces to facilitate squeeze control of flow through the cassette tubes, and push/snap on-off cassette connections for connecting tubing to facilitate rapid deployment and re-deployment of the suction-irrigation device. Through the efficacious use of rollers, wedges and springs, improved flow control is achieved while enhancing the feel associated with operation and reducing required finger pressure.

OBJECTS AND FEATURES OF THE INVENTION

It is one general object of the invention to improve suction-irrigation devices.

It is another object of the invention to increase ease and rapidity with which a suction-irrigation device can be made ready for repeated uses.

It is yet another object of the invention to improve feel while controlling fluid flow through a suction-irrigation device.

It is still another object of the invention to reduce finger pressure required to control fluid flow through the suction-irrigation device.

Accordingly, in accordance with one feature of the invention, a generally symmetrical housing is employed, and in-line trumpet valves are disposed along the longitudinal axis of the housing, thus rendering the unit equally usable in either the right or left hand.

In accordance with another feature of the invention, the principal parts of the housing are hinged for ease of opening while including interior surfaces that are contoured to form-fit with the exterior surfaces of the disposable tri-tubular cassette that fits therewithin, thus facilitating assembly use and re-use.

In accordance with still another feature of the invention, the aforementioned trumpet valve elements are each spring loaded and fitted with a roller and an engaging inclined plane or wedge which moves a connected member into and out of engagement with a predetermined portion of a corresponding one of the tri-tubular cassette tubes, thus facilitating control and adding to user feel associated with flow control.

These and other objects and features of the invention will be apparent from the following description, by way of example of a preferred embodiment, with reference to the drawing.

BRIEF DESCRIPTION OF THE DRAWING

FIG. 3 is a side elevation view illustrating the tri-tubular structure of the disposable cassette for the suction-irrigation device;

FIG. 4 is a sectional view through the disposable cassette taken along the section lines 4—4 of FIG. 3;

FIG. 5 is a sectional view taken along the section lines 5—5 of FIG. 2;

FIG. 6 is a partial sectional view through the suction-irrigation device taken along the section lines 6—6 of FIG. 2;

FIG. 7 is another partial sectional view through the suction-irrigation device taken along the section lines 7—7 of FIG. 2;

FIG. 8 is a detail view illustrating the geometry of the rear mounted trumpet valve actuating piston of FIGS. 2 and 5;

FIG. 9 is a detail view illustrating the geometry of the forward mounted trumpet valve actuating piston of FIGS. 2 and 5;

FIG. 10 is a sectional view taken along section lines 10—10 of FIG. 5 illustrating the camming action of the proximal trumpet valve; and FIG. 11 is a sectional view taken along section lines 11—11 of FIG. 5 illustrating the camming action of the distal trumpet valve.

DESCRIPTION OF A PREFERRED EMBODIMENT

Figure 1:
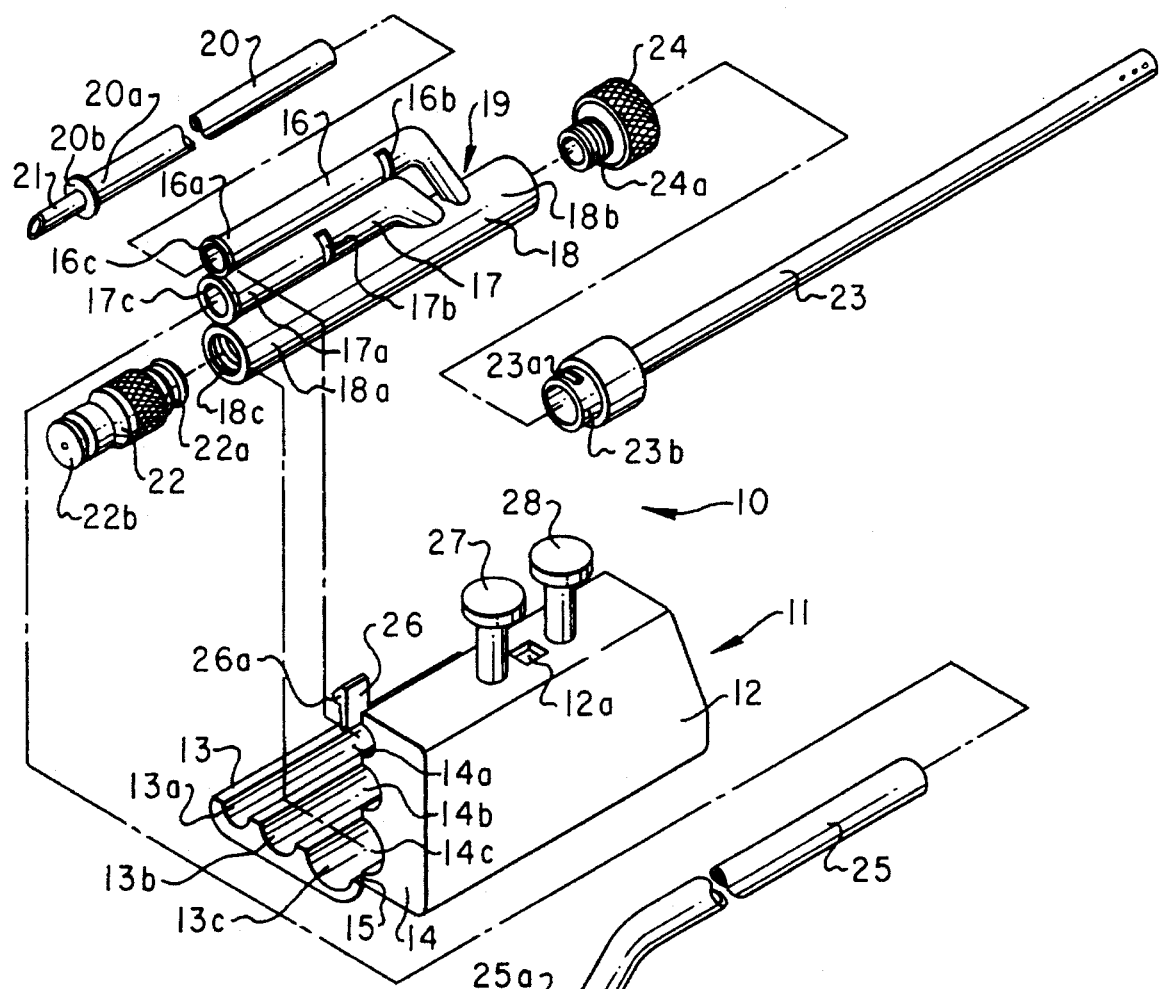
FIG. 1 is an exploded view of the suction-irrigation device according to the invention illustrating the instrument with its access door in the open position.

Now turning to the drawing, and more particularly FIG. 1 thereof, it will be seen to be a perspective view of the inventive suction-irrigation device 10, partially exploded to facilitate description thereof. It is seen to include an exterior housing 11 having a principal housing portion 12 and an attached hinged closure member 13. The proximal end 14 includes three semi-circular spaces 14a, 14b and 14c which, when closure member 13 is swung upwardly about its hinge 15, mate with corresponding semi-circular spaces 13a, 13b and 13c to form circular openings tightly enclosing proximal portions 16a, 17a and 18a of tubes 16, 17 and 18 of tri-tubular disposable insert 19. As will be described in greater detail below, at least certain parts of tubes 16 and 17 of disposable insert 19 are resilient and may be made of any of a variety of well-suited surgical materials such as silicone rubber surgical tubing. Adapted for frictional engagement with and insertion into proximal end 16a of tube 16 is a mating tubular member 20 which is fitted at its proximal end 20a with a quick connect/disconnect collar 20b to which irrigating fluid line 21 is connected in the conventional manner. It should be noted at this point that even though the direction of flow of irrigating fluid is toward the patient, it is possible for the line to become contaminated by reverse flow, capillary action, surface migration or the like unless preventive precautions are taken. Therefore, in order to avoid contamination of the irrigating fluid line 21 by blood, stool or other body fluids of the patient, a conventional check valve may be interposed in the line 21, collar connector 20b or tubular member 20.

Before proceeding further with the description of FIG. 1, it may be helpful to consider carefully the tri-tubular disposable insert 19. As mentioned above, it is comprised of the three tubes 16, 17 and 18 which are internally connected together near the distal end 18b of tube 18 (FIG. 3) so as to provide for commonality of fluid flow therewithin. Tube 18 is preferably made of rigid or semi-rigid material as may be portions of tubes 16 and 17. However, at least in regions of tubes 16 and 17 as depicted by rectangles 16b and 17b, tubes 16 and 17 will either be flexible or will include a flexible portion that is adapted for being pinched so as to close the passageways through tubes and One of the reasons why tube 18 preferably is made of rigid or semi-rigid material is so as to facilitate the provision of threads in both its proximal and distal ends. In the proximal end 18a, female threads 18c are provided to mate with closure plug 22 which is fitted at its forward end with male engaging threads 22a. Closure plug 22 is provided at its proximal end with a closure member 22b that serves to seal the proximal end when in place but which may be removed so as to open up a passage therethrough. Accordingly, provision is made for either sealing the proximal end 18a of tube 18 or opening it so that a surgical instrument may be inserted therein to pass through tube 18 and surgical member 23 to a patient's interior, thus facilitating performance of certain surgical procedures.

At distal end 18b of the tri-tubular disposable insert 19, internal female threads are also provided so engage with matching male threads 24a of adapter collar 24. Adapter collar 24 is conventional and preferably includes a quick connect/disconnect feature as represented by the semi-circular projection 23a on proximal end Further reference to FIG. 1 reveals suction coupling tube 25 that is adapted for insertion into and frictional engagement with tube 17. Suction coupling tube 25 is provided as an interface between tube 17 of tri-tubular disposable insert 19 and a conventional source of suction (not shown). Since, as will be recognized by those skilled in the art, problems associated with potential contamination are particularly acute in suction lines, it is contemplated that a sterile fluid trap will be interconnected in the suction line leading from tube 25 to the conventional suction source. Although such fluid trap may be used repeatedly provided adequate sterilization procedures are followed, it is contemplated that relatively inexpensive fluid traps will be used with the suction-irrigation device described herein, thus reducing time and effort in making ready for the next patient. It will also be evident that although tube 25 is shown as fitted with a collar 25a, such is optional and may readily be omitted if desired.

Now returning to the hinged closure member 13, it will be observed that it is fitted with a conventional flexible tang 26 that is fitted with a projection 26a adapted for projecting into opening 12a and thus locking closure member 13 to principal portion 12 when member 13 is swung upwardly about its hinge 15 into a closed position. As will be evident to those skilled in the art, a sideways deflection of tang 25 under manual pressure will disengage it from opening 12a, thus freeing member 13 to be swung downwardly to the position shown in FIG. 1.

Finally, in FIG. 1 there are seen a pair of in-line trumpet valve actuating buttons 27 and 28. As depicted, button 27 is proximal and controls suction, whereas button 28 is distal and controls irrigation. Operation of these buttons and the corresponding opening and closing of passageways through tubes 16 and 17 will be evident from the description below.

Figure 2:
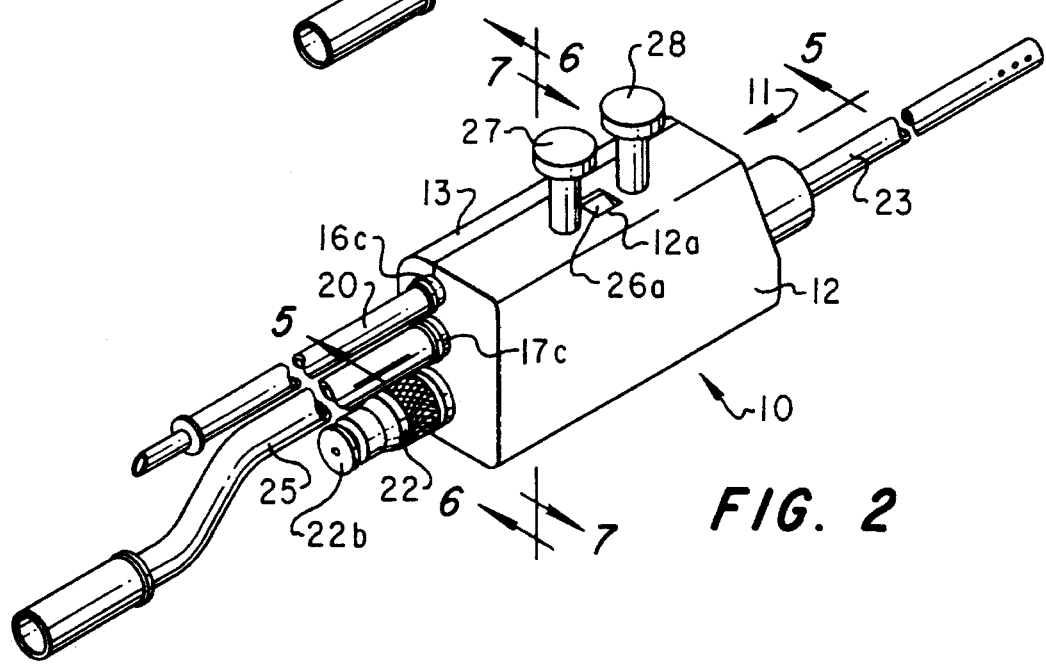
FIG. 2 is a perspective view illustrating the suction-irrigation device of FIG. 1 when assembled.

Now turning to FIG. 2, it will be seen to depict the suction-irrigation device 10 of FIG. 1 in its assembled and locked condition. Thus, tang projection 26a is residing within recess 12a. Collars 16c and 17c are shown in place to aid in correctly positioning the tri-tubular disposable insert 19 in its correct position within the housing 11. Removable closure member 22b is shown in place; and to identify the sections of FIGS. 5, 6 and 7, pairs of conventional section lines are included.

As mentioned above, FIG. 3 depicts the tri-tubular disposable insert 19 in detail. There, in addition to the parts described above for FIG. 3, there are collars 16c and 17c and the internal female threads lad provided in the distal end lab of tubular portion 18. The confluence of tubes 16, 17 and 18 is also shown as at points 16d and 17d where the inner passageways are joined together to provide fluid communication therebetween. Of course, it will be evident to those skilled in the art that press fittings or other known types of threadless connectors could be substituted for the threaded connections.

As will be observed from further reference to FIG. 3, FIG. 4 is a sectional view taken along the section lines 4—4 which, it will be observed, pass through regions 16b and 17b. It will be recalled that regions 16b and 17b represent resilient regions of tubes 16 and 17, resilient regions provided so that they are readily deformable to the extent that flow therethrough may be readily and entirely pinched off by the actuating mechanism described In connection with FIGS. 5–11. Accordingly, it is contemplated hereby that tubes 16 and 17 may be made mostly or entirely of resilient material through which flow can be pinched off entirely after which the material will return to its original condition when pinching effort is removed, material such as surgical tubing; or the principal portions of tubes 16 and 17 may be of non-resilient material and only a part such as that exposed at regions 16b and 17b be fully pinchable. Regardless of which of these alternatives is employed, it is important that a portion of tubes 16 and 17 be capable of being pinched off so as to control flow of liquids or gaseous fluids therethrough.

In accordance with the preferred embodiment, distal portions of members 20 and 25 are made of resilient material and are exposed through regions 16b and 17b which are formed in the walls of tubes 16 and 17 respectively, thereby permitting pinching forces to be applied thereto through such exposed regions. According to such preferred embodiment, the sectional view of FIG. 4 depicts a portion of tube 20 exposed through opening 16b, and a portion of tube 25 exposed through opening 17b. As is hereinafter described, provision is made to separately and individually apply lateral forces to these exposed regions through apertures 16b and 17b so separately control pinching and consequential fluid flow through tubes 16/20 and 17/25.

Now turning to FIG. 5, a section taken through the suction-irrigation device along section lines 5—5 of FIG. 2 will be seen. There, in addition to the above-described members, are the inner extensions 27a and 28a of trumpet valve actuating buttons 27 and 28 which are adjoined to lower camming portions 27b and 28b respectively. At this point it should be noted that actuating buttons 27 and 28, together with their extensions 27a /b and 28a/b may be of one piece metal or molded plastic, or they may be separate pieces that are fastened together into a relatively rigid assembly. Such are shown in detail in FIGS. 8 and 9 respectively where their preferred geometries and camming surfaces are more readily observable.

In FIG. 8, camming surfaces 27c/28c are seen to extend upwardly at about a 45 degree angle with respect to essentially horizontal surfaces 27d/28d thus causing cylindrical follower pins 29 and 30 to move at right angles thereto as trumpet valve mechanisms 27 and 28 ride up and down in tracks 27f/28f under finger pressure imparted by the suction-irrigation device user. Such will more readily observed in connection with the description below for FIGS. 10 and 11. In addition to the camming surfaces, there are provided apertures 27e and 28e parts of which are just visible in FIGS. 8 and 9 but which are more readily observed in FIG. 5. These apertures are provided so that the camming followers 31 and 32 may respectively extend therethrough and impart pinching forces to the portions of tubes 20 and 25 that are exposed through apertures 16b and 17b as described above.

Also seen in FIG. 5 are biasing springs 33 and 34 which are provided to normally impart pinching pressure to the resilient tubes 20 and 25 through cam followers 31 and 32. As will be observed from inspection of FIGS. 5 and 10/11, extending portions 33a and 34a of biasing springs 33 and 34 extend through apertures in cam followers 31 and 32 so as to normally urge them inwardly to pinch off the adjacent tubes 20 and 25.

Before proceeding to a more detailed description of the foregoing camming assemblies, reference is now made to FIGS. 6 and 7 which, it will be recalled are taken along the section lines 6—6 and 7—7 of FIG. 2. As will be observed from the Figures, section lines 6—6 and 7—7 are taken essentially through the suction-irrigation device 10 along hinge 15, and the tri-tubular disposable insert 19 and its connections are shown in phantom. FIG. 6 shows the interior surfaces of closure member 13 (e.g., 13a, 13b and 13c) illustrating the interior surfaces that conform to corresponding exterior surfaces of tubes 16, 17 and 18.

FIG. 7 shows those interior surfaces of principal housing portion 12 that correspondingly conform to exterior surfaces of tubes 16, 17 and 18 and including regions 27e and 28e as described above.

As mentioned above, FIGS. 10 and 11 are depict sections taken through the drawing of FIG. 5 along section lines 10—10 and 11—11 respectively. They show details of the trumpet valve actuating assemblies including valve actuating buttons 27 and 28 respectively. Turning first to FIG. 10, it will be seen to depict actuating button 27 shown in its extended (valve closed) position in solid lines and in its depressed (valve open) position in phantom. It includes an upper enlarged portion 279 attached to extending shaft portion 27h, the interior portion of which is designated 27a. When button 27 is in its normal (extended) position as shown in solid lines, the aforementioned lateral thrust imparted by biasing spring 33 forces cam follower 31 into its valve closed position, thus deforming tubular section 17b as shown to pinch it off. As vertical force represented by arrow 35 increases, member 27 moves downwardly with the result that cam follower pin 29 rides on camming surface 27c thus forcing it outwardly (because of the inclination of surface 27c), thus moving cam follower horizontally into the position shown in phantom and releasing pinching pressure on tubular section thus permitting the resiliency of the tube to cause it to resume its normal, or open, condition. (It's passageway is shown as open in FIG. 11 because of the location of section lines 11—11.

Operation of the valve assembly of FIG. 11 is generally similar to that of FIG. 10 except that in FIG. 11 opening and closing of tubular section 16b. There, in FIG. 11, it is seen that actuating button 28 shown in its extended (valve closed) position in solid lines and in its depressed (valve open) position in phantom. It includes an upper enlarged portion 28g attached to extending shaft portion 28h, the interior portion of which is designated 28a. When button 28 is in its normal (extended) position as shown in solid lines, the aforementioned lateral thrust imparted by biasing spring 34 forces cam follower 32 into its valve closed position, thus deforming tubular section 16b as shown to pinch it off. As vertical force represented by arrow 36 increases, member 28 moves downwardly with the result that cam follower pin 30 rides on camming surface 28c thus forcing it outwardly (because of the inclination of surface 28c), thus moving cam follower horizontally into the position shown in phantom and releasing pinching pressure on tubular section 16b, thus permitting the resiliency of the tube to cause it to resume its normal, or open, condition. (It's passageway is shown as open in FIG. 10 because of the location of section lines 10—10.) Thus, cam follower 32 in FIG. 11 generally corresponds to follower 31 in FIG. 10 and operates in a similar manner as cam follower pin 30 rides on camming surface 28c.

As previously mentioned, one of the features of the invention lies in the ease with which it can be made ready for repeated use. Connecting implements and hoses are disconnected, the housing is opened, and the disposable insert is discarded and a fresh one installed, thus avoiding the time-consuming and expensive steps of sterilizing the entire suction-irrigation device.

It will now be evident that there has been described herein, a discardable-insert suction-irrigation device having improved control, feel and other handling qualities; that it is relatively simple and inexpensive in design, is neither right or left-handed, and that it is easy and cost-effective to produce and use, thus contributing to its attractiveness and desirability.

Although the inventions hereof have been described by way of a preferred embodiment, it will be evident that other adaptations and modifications may be employed without departing from the spirit and scope thereof. For example, an additional tubular channel could be included together with an additional control trumpet valve. Alternatively, one part of the housing may be formed integrally with the disposable tri-tubular cassette and disconnectably attached to the remaining parts of the housing by any of a plurality of quick-disconnect attachments well known in the art.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A suction-irrigation device comprising:
   (a) a unitary disposable tri-tubular cassette having a single output and a plurality of elongated input channels in interior fluid communication with said output all of said channels lying essentially in a first plane and, over a major portion of their lengths being axially parallel to each other;
   (b) an elongated housing having a principal elongated central axis and being formed in a plurality of parts, at least two of said parts having interior surfaces, one of said interior surfaces being adapted for receiving, engaging and holding said cassette; and
   (c) a plurality of trumpet valve controllers generally disposed along said central axis, said trumpet valve controllers severally engaging different ones of said input channels normally to squeeze said channels and prevent fluid flow therethrough, and when individually operated, to selectively reduce said squeeze on said channels and selectively control fluid flow therethrough.

2. A suction-irrigation device according to claim 1 further including hinge means connecting together said at least two of said parts.

3. A suction-irrigation device according to claim 1 in which said first plane is displaced from said central axis within said elongated housing.

4. A suction-irrigation device according to claim 1 in which said first plane is displaced and parallel to said central axis within said elongated housing.

5. A suction-irrigation device comprising:
   (a) a disposable multi-tubular cassette having a single output and a plurality of input channels in interior fluid communication with said output all of said channels lying essentially in a first plane;
   (b) an elongated housing having a principal elongated central axis and being formed in a plurality of parts, at least two of said parts having interior surfaces, one of said interior surfaces being adapted for receiving, engaging and holding said cassette; and
   (c) a plurality of trumpet valve controllers generally disposed along said central axis, said trumpet valve controllers severally engaging different ones of said input channels normally to squeeze said channels and prevent fluid flow therethrough, and when individually operated, to selectively reduce said squeeze on said channels and selectively control fluid flow therethrough, said trumpet valves each including an exterior end connected with a camming pin and an inclined plane normally engaging said camming pin, whereby, when said piston is depressed, said camming pin is correspondingly moved along said inclined plane thereby correspondingly moving said camming pin in a direction transverse to the longitudinal axis of said piston.

6. A suction-irrigation device according to claim 5 further including a plurality of springs severally interconnected with said piston portions thereby to spring load said piston portions into normally fluid interrupting positions.

7. A suction-irrigation device according to claim 5 further including a plurality of cam followers severally interconnected with said camming pins.

8. A suction-irrigation device according to claim 6 further including a plurality of cam followers severally interconnected with said camming pins.

9. A suction-irrigation device according to claim 8 in which parts of said cam followers normally engage preselected portions of two of said channels and wherein said springs are interconnected with said cam followers normally to urge said cam followers into tube deformation positions to squeeze closed said two of said channels.

10. A suction-irrigation device comprising:
    (a) a tri-tubular member having a single output and a plurality of elongated input channels in interior fluid communication with said output, all of said channels lying essentially in a first plane and, over a major portion of their
    (b) an elongated housing having a principal elongated central axis and being formed in a plurality of parts, at least two of said parts having interior surfaces, one of said interior surfaces being adapted for engaging said multi-tubular member and a second of said two of said parts being formed integrally with said multi-tubular member; and
    (c) a plurality of trumpet valve controllers generally disposed along said central axis, said trumpet valve controllers severally engaging different ones of said input channels normally to squeeze said channels and prevent fluid flow therethrough, and when individually operated, to selectively reduce said squeeze on said channels and selectively control fluid flow therethrough.

11. A suction-irrigation device according to claim 10 further including quick-disconnect means for disconnectably connecting together said at least two of said parts.

12. A suction-irrigation device according to claim 10 wherein said second of said two of said parts is disposable.

13. A suction-irrigation device according to claim 10 in which said first plane is displaced from said central axis within said elongated housing.

14. A suction-irrigation device according to claim 10 in which said first plane is displaced and parallel to said central axis within said elongated housing.

15. A suction-irrigation device comprising:
    (a) a multi-tubular member having a single output and a plurality of input channels in interior fluid communication with said output, all of said channels essentially in a first plane;
    (b) an elongated housing having a principal elongated central axis and being formed in a plurality of parts, at least two of said parts having interior surfaces, one of said interior surfaces being adapted for engaging said multi-tubular member and a second of said two of said parts being formed integrally with said multi-tubular member; and (c) a plurality of trumpet valve controllers generally disposed along said central axis, said trumpet valve controllers severally engaging different ones of said input channels normally to squeeze said channels and prevent fluid flow therethrough, and when individually operated, to selectively reduce said squeeze on said channels and selectively control fluid flow therethrough, said trumpet valves each including an exterior end adapted for manual manipulation and an interior end connected with a camming pin and an inclined plane normally engaging said camming pin, whereby, when said piston is depressed, said camming pin is correspondingly moved along said inclined plane thereby correspondingly moving said camming pin in a direction transverse to the longitudinal axis of said piston.

16. A suction-irrigation device according to claim 15 further including a plurality of springs severally interconnected with said piston portions thereby to spring load said piston portions into normally fluid interrupting positions.

17. A suction-irrigation device according to claim 15 further including a plurality of cam followers severally interconnected with said camming pins.

18. A suction-irrigation device according to claim 16 further including a plurality of cam followers severally interconnected with said camming pins.

19. A suction-irrigation device according to claim 18 in which parts of said cam followers normally engage preselected portions of certain of said channels and wherein said springs are interconnected with said cam followers normally to urge said cam followers into tube deformation positions to squeeze closed said certain of said channels.

20. A suction-irrigation device according to claim 18 in which parts of said cam followers normally engage preselected portions of two of said channels and wherein said springs are interconnected with said cam followers normally to urge said cam followers into tube deformation positions to squeeze closed said two of said channels.

* * * * *